(12) United States Patent
Kotian (10) Patent No.: US 10,062,466 B2
(45) Date of Patent: Aug. 28, 2018

(54) APPARATUS, SYSTEM AND METHOD FOR REDUCING RADIATION SCATTER IN AN IMAGING SYSTEM

(71) Applicant: General Electric Company, Schenectady, NY (US)

(72) Inventor: Francois Kotian, Villepreux (FR)

(73) Assignee: General Electric Company, Schenectady, NY (US)

( * ) Notice: Subject to any disclaimer, the term of this patent is extended or adjusted under 35 U.S.C. 154(b) by 335 days.

(21) Appl. No.: 15/087,126

(22) Filed: Mar. 31, 2016

(65) Prior Publication Data

US 2017/0287582 A1    Oct. 5, 2017

(51) Int. Cl.
| | |
|---|---|
| *G21K 1/00* | (2006.01) |
| *G21K 1/06* | (2006.01) |
| *A61B 6/00* | (2006.01) |
| *G21K 1/02* | (2006.01) |
| *A61B 6/03* | (2006.01) |

(52) U.S. Cl.
CPC ............. *G21K 1/06* (2013.01); *A61B 6/032* (2013.01); *A61B 6/4085* (2013.01); *A61B 6/4291* (2013.01); *A61B 6/4411* (2013.01); *A61B 6/4494* (2013.01); *A61B 6/467* (2013.01); *A61B 6/5282* (2013.01); *A61B 6/54* (2013.01); *G21K 1/02* (2013.01); *A61B 6/03* (2013.01); *A61B 6/4441* (2013.01)

(58) Field of Classification Search
CPC ......... A61B 6/4291; A61B 6/03; A61B 6/032; A61B 6/4085; A61B 6/4225
See application file for complete search history.

(56) References Cited

U.S. PATENT DOCUMENTS

| | | | |
|---|---|---|---|
| 6,244,507 | B1 | 6/2001 | Garland et al. |
| 6,470,072 | B1 | 10/2002 | Johnson |
| 8,172,461 | B2 | 5/2012 | Liu et al. |
| 8,634,517 | B2 | 1/2014 | Maack |
| 2002/0090055 | A1 | 7/2002 | Zur et al. |
| 2002/0126800 | A1 | 9/2002 | Matsumoto et al. |

(Continued)

FOREIGN PATENT DOCUMENTS

CN    103961116 A    8/2014

OTHER PUBLICATIONS

Extended European Search Report and Opinion issued in connection with corresponding EP Application No. 16204030.7 dated Aug. 17, 2017.

*Primary Examiner* — Don Wong
(74) *Attorney, Agent, or Firm* — Grogan, Tuccillo & Vanderleeden, LLP (57) ABSTRACT

An apparatus for reducing radiation scatter in an imaging system having an operational slot for receiving an anti-scatter grid. The apparatus includes an imaging system component having at least one storage slot formed therein for selectively storing an anti-scatter grid when the grid is not in the operational slot of the imaging system. The apparatus further includes an operational slot sensor configured to detect the presence of an anti-scatter grid and/or an imaging property of a grid in the operational slot. The system allows an operator to select an appropriate anti-scatter grid for use in the imaging system from one or more anti-scatter grids that are located within the operational and/or storage slots of the imaging system.

27 Claims, 6 Drawing Sheets

(56) References Cited

U.S. PATENT DOCUMENTS

2010/0002831 A1* 1/2010 Maack .................... A61B 6/06
　　　　　　　　　　　　　　　　　　　　　　378/16
2013/0188780 A1　7/2013　Hruschka et al.
2014/0014828 A1　1/2014　Bredno et al.

* cited by examiner

APPARATUS, SYSTEM AND METHOD FOR REDUCING RADIATION SCATTER IN AN IMAGING SYSTEM

BACKGROUND

Technical Field

Embodiments of the invention relate generally to imaging and more specifically reducing radiation scatter in an x-ray imaging system.

Discussion of Art

During medical diagnostic radiography processes, x-rays are directed toward an object from an x-ray source. When x-rays are used to create an image of an object, a portion of the radiation passes directly through the object from the x-ray source and onto an x-ray detector or film to create an image. Some of the direct radiation is differentially absorbed by the object, which creates an image of the object on the detector or film. A portion of the radiation, however, is scattered and arrives at the x-ray detector at an angle that deviates significantly from its original path from the x-ray source. As will be appreciated, this scattered radiation reduces contrast of the radiograph image and can potentially affect image quality.

Many medical x-ray imaging systems use a post-patient collimation device to reduce the scattered radiation reaching the detector. Such imaging systems often use a removable x-ray grid, i.e., an "anti-scatter grid," as the collimation device. Anti-scatter grids are typically fabricated from thin strips of x-ray absorbing material, e.g., lead, that are arranged in a geometric pattern to absorb scattered radiation. These grids also include a non-absorbent spacer material between the x-ray absorbing strips that allows direct radiation to pass through the grid.

The strips in an anti-scatter grid, however, are all directed or angled to a fixed distance. That is, the grids have a fixed focal distance, i.e., a focal length, from the x-ray source. Ideally, the x-ray source is positioned from the grid/detector assembly at this focal length to achieve optimal radiograph results. In many x-rays systems, however, the x-ray source to detector distance, ("SID"), is variable and can be greater or less than the fixed focal length of the grid. For example, in interventional x-ray imaging systems, the SID varies typically from 85 cm to 125 cm. Given this range, in many such systems, a general-purpose anti-scatter grid is utilized at a fixed focal length typically of 100 cm. The further away the grid/detector assembly is from the grid focal length, however, the more the grid attenuates primary radiation at the periphery of the field of view.

In certain types of imaging modes, such as Cone Beam CT mode "CBCT") imaging, the use of specific grids that are focused at a particular SID that may be different from general purpose grids would be highly desirable. Moreover, in certain circumstances, such as pediatric or extremity imaging, it may be desirable to image a subject without a grid. As will be appreciated, obtaining optimal image quality and/or radiation dose in view of these considerations may necessitate replacing or substituting the anti-scatter grid during operation.

What is needed, therefore, is an apparatus and method that facilitates the use of multiple anti-scatter grids during operation of an imaging system.

BRIEF DESCRIPTION

In an embodiment, an apparatus for reducing radiation scatter in an imaging system having an operational slot for receiving an anti-scatter grid, includes an imaging system component having at least one storage slot formed therein for selectively storing an anti-scatter grid when the grid is not in the operational slot of the imaging system. The apparatus further includes an operational slot sensor configured to detect the presence of an anti-scatter grid and/or an imaging property of a grid in the operational slot. The system allows an operator to select an appropriate anti-scatter grid for use in the imaging system from one or more anti-scatter grids that are located within the operational and/or storage slots of the imaging system.

In another embodiment, an imaging system includes a radiation source, a radiation detector and an operational slot located between the radiation source and radiation detector, the operational slot configured to receive an anti-scatter grid. The system further includes at least one storage slot formed in a imaging system component, the storage slot configured to receive and store an anti-scatter grid when the device is not in use in the operational slot and an operational slot sensor configured to detect the presence of an anti-scatter grid and/or an imaging property of a grid in the operational slot. The system allows an operator to select an appropriate anti-scatter grid from one or more anti-scatter grids that are located within the operational and/or storage slots of the imaging system.

In yet another embodiment, a method of reducing radiation scatter in an imaging system having operational and storage slots for selectively receiving anti-scatter grids includes assessing a parameter of an operational slot via an operational slot sensor, determining whether the assessed parameter is appropriate for a preselected imaging mode of the imaging system, and selecting an appropriate anti-scatter grid, if required, from one or more anti-scatter grids located in the operational and/or storage slots of the imaging system, based on the assessed parameter.

DRAWINGS

The present invention will be better understood from reading the following description of non-limiting embodiments, with reference to the attached drawings, wherein below.

DETAILED DESCRIPTION

Reference will be made below in detail to exemplary embodiments of the invention, examples of which are illustrated in the accompanying drawings. Wherever possible, the same reference characters used throughout the drawings refer to the same or like parts, without duplicative description.

As used herein, the terms "substantially," "generally," and "about" indicate conditions within reasonably achievable manufacturing and assembly tolerances, relative to ideal desired conditions suitable for achieving the functional purpose of a component or assembly. As used herein, "electrically coupled, "electrically connected" and "electrical communication" means that the referenced elements are directly or indirectly connected such that an electrical current may flow from one to the other. The connection may include a direct conductive connection (i.e., without an intervening capacitive, inductive or active element), an inductive connection, a capacitive connection, and/or any other suitable electrical connection. Intervening components may be present.

Additionally, while the embodiments disclosed herein are described with respect to x-ray imaging systems, they are not limited to a particular type of x-ray system and embodiments are applicable to stationary or mobile systems. Moreover, it is to be understood that embodiments of the present invention are potentially applicable to other types of imaging systems. Furthermore, embodiments of the present invention are not limited to analyzing human tissue and may be utilized to analyze other materials.

Figure 1:
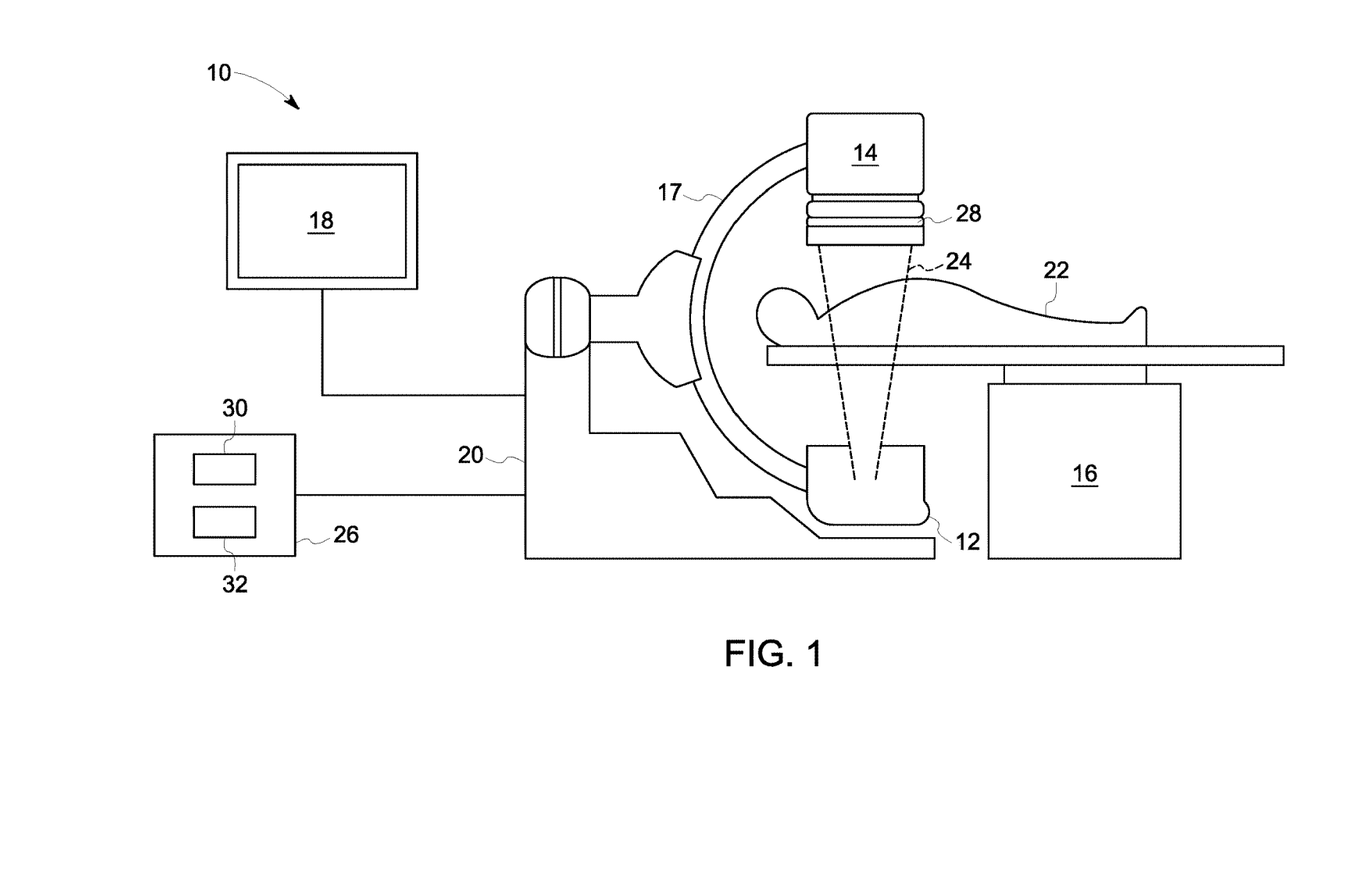
FIG. 1 is a simplified schematic diagram of an imaging system that may be utilized with certain embodiments of the present invention.

Referring now to FIG. 1, a simplified schematic of an x-ray imaging system 10 is shown. The system 10 generally includes a radiation source 12, a detector 14, and a table 16. In the depicted system, the radiation source 12 is mounted on an arm 17 of a gantry 20. In certain embodiments, however, the radiation source 12 may be movably secured to another surface of system 10 or the imaging room. Moreover, in aspects, the gantry 20 may be stationary and fixed to the floor of an imaging room, or movable, e.g., wheeled, such that the radiation source 12 and detector 14 may be moved from one imaging room to another. In embodiments where the gantry 20 is fixed, the table 16 may be movable to facilitate position of a subject 22 relative to the radiation source 12. The radiation source 12 may also be mechanically movable/positionable relative to the gantry 20 to facilitate imaging.

As will be appreciated, the detector 14 may also be fixed or movable. In this regard, the detector may be movably secured to the gantry 20 such that the detector 14 is spaced apart from the radiation source 12 and movable, e.g., rotatable, with the radiation source 12 relative to the table 16 and subject 22.

As shown, the system 10 also includes a collimator/anti-scatter grid 28. In use, the subject 22 is situated between the radiation source 12 and the detector 14. The radiation source 12 is then positioned such that it projects a primary radiation beam 24 through an area of interest in the patient 22 and into the anti-scatter grid 28 The grid 28 removes scattered photons which allowing primary beams photons to pass through to the detector 14. The detector 14 converts x-ray photons to electric signals, which are processed to reconstruct and generate one or more images that are communicated to a controller 26, which in some cases may be displayed on screen 18. In embodiments, the detector 24 may be digital, i.e., captures radiographic images in digital form, although the invention is not limited to the same. As will be appreciated, the screen 18 may be suspended from a ceiling of an imaging room or integrated into a component of the imaging system 10.

The controller 26 includes at least one processor 30 and at least one memory device 32 and is in communication with both the detector 14 and the display screen 18. In embodiments, the controller 26 may be in further communication with the radiation source 12, the detector 14, the anti-scatter grid and/or the table 16. An imaging program/application may be stored in the at least one memory device that, when loaded into the at least one processor, adapts the controller 26 to process the images received from the detector 14. In embodiments, the imaging program may further adapt the controller 26 to control and coordinate the detector 14, the radiation source 12, the anti-scatter grid 28, and any positioning equipment associated therewith.

Figure 2A:
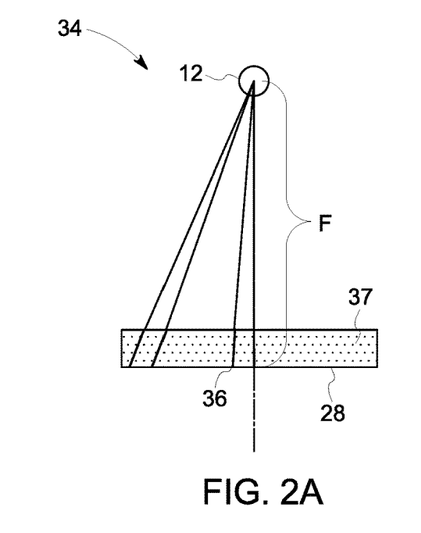
FIGS. 2A-2C are diagrams depicting relationships between SID of a radiation source and focal length of an anti-scatter grid.

As mentioned, anti-scatter grids are typically manufactured from thin strips of x-ray absorbing material, such as lead, that are arranged in a geometric pattern to absorb scattered radiation. Grids also include a low absorption spacer material 37 between the x-ray absorbing strips 36 that allows most of the primary radiation to pass through the grid (FIG. 2A). In addition to focal distance, which is determined by the angle of the strips, grids are also characterized by the grid ratio, grid frequency and focal range. The grid ratio is a measure of the height of the strip to the interspace distance. The grid frequency is a measure of the number of grid lines per unit distance. Focal range is an indicator of the flexibility of grid positioning distance, and is a function of the grid ratio and frequency.

Figure 2B:
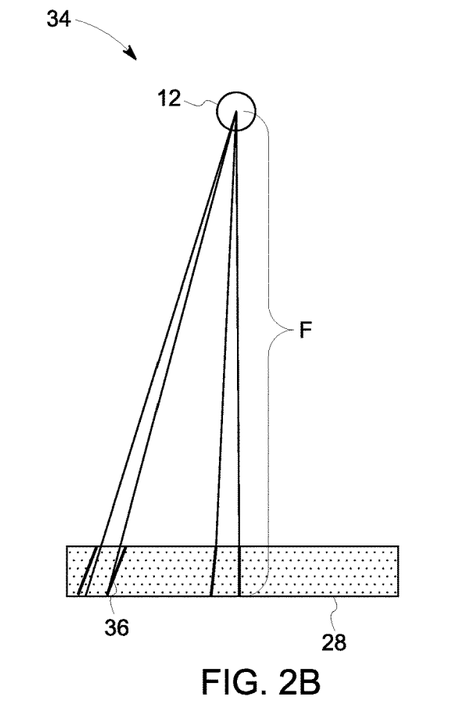
Figure 2C:
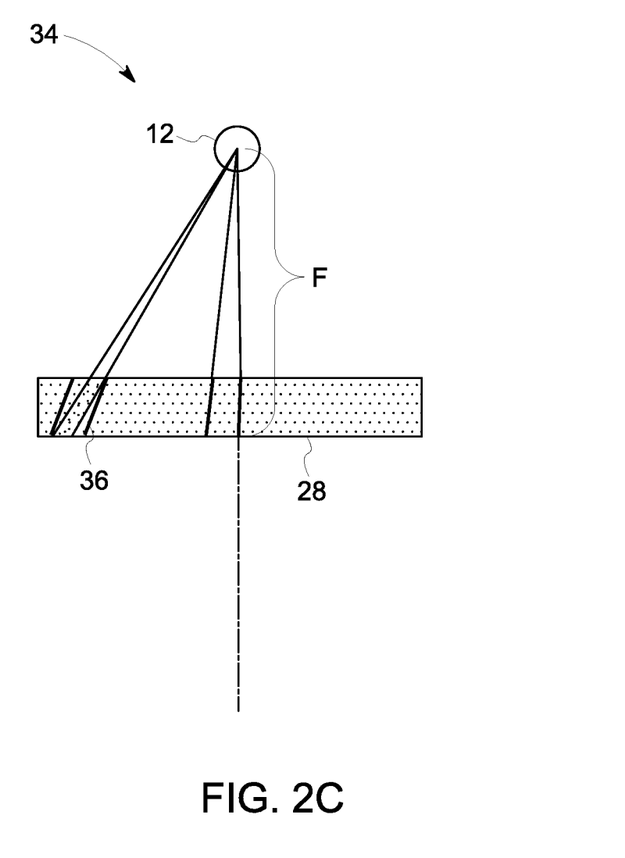

Referring now to FIGS. 2A-2C, relationships between SID of a radiation source 12, and the focal length f of an anti-scatter grid 28, are depicted. FIG. 2A illustrates a configuration where the SID of the source 12 is equal to or compatible with the focal length f of the grid 28. As shown, the primary x-ray beams 34 are substantially aligned with the strips 36 of the grid 28. In contrast, in FIGS. 2B and 2C, which depict configurations where the SID is substantially greater than and less than grid 28 focal length f respectively, the primary x-ray beams 34 are misaligned relative to the grid 28. As a result, the grid 28 can significantly attenuate the primary beam at the periphery of the field of view potentially leading to signal loss, which affects image quality.

As mentioned, many interventional x-ray systems have an SID that varies typically from 85 cm to 120 cm. Many such systems utilize a grid having a focal length of about 100 cm. These "general-purpose" grids are suitable for use in the aforementioned SID range, as the grids have a focal range, which allows for acceptable imaging. In certain imaging modes, however, such as CBCT imaging, specific grids that are optimized for a particular SID may be desirable. These grids, however, may have a focal range that is not amenable for use across the entire SID range employed in interventional imaging. Moreover, the use of general-purpose grids in CBCT imaging may result in less than optimal image quality, as CBCT imaging requires a large fixed SID as the gantry rotates about a patient. Furthermore, in certain circumstances, such as pediatric or extremity imaging, it may be desirable to image a subject without a grid.

In view of the above, it will be appreciated that different imaging situations may require different grids (or no grid) to create images of acceptable quality. This, in turn, may necessitate replacing or substituting an anti-scatter grid during operation of the imaging system. Embodiments of the invention facilitate the use of multiple grids during operation.

Figure 3:
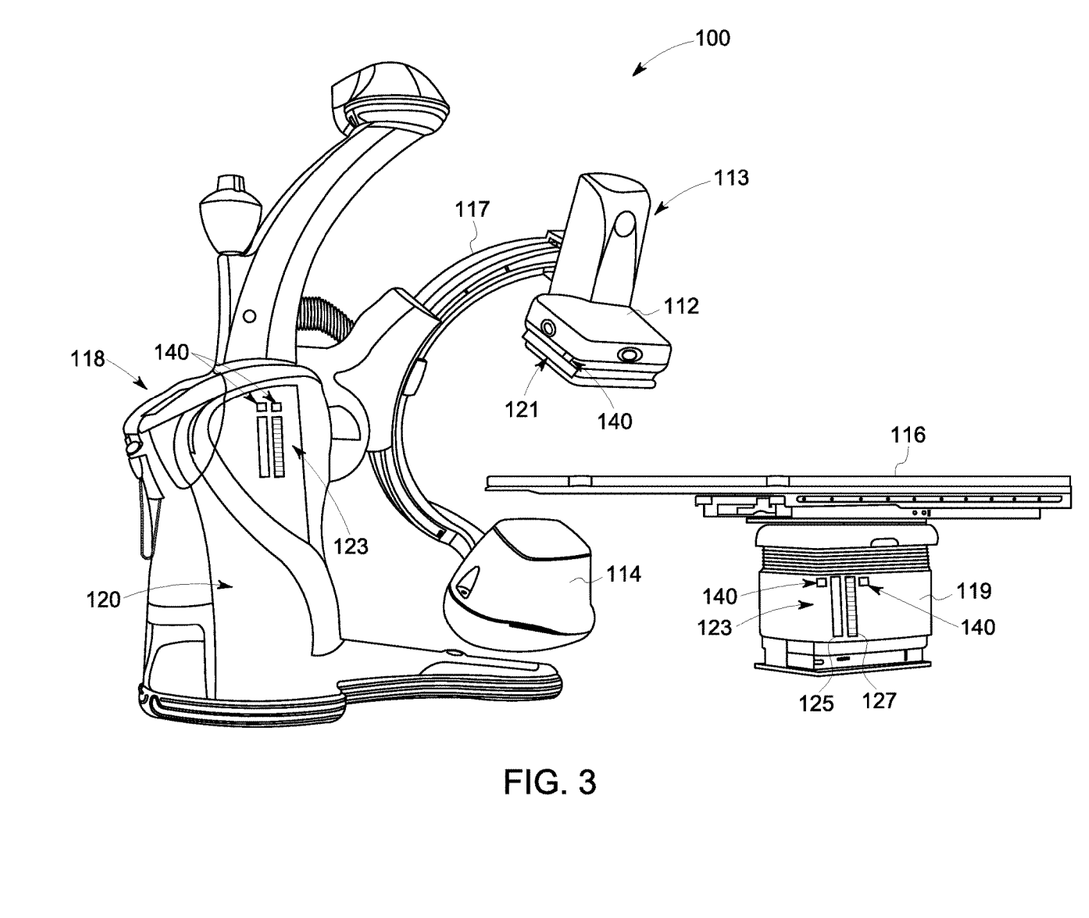
FIG. 3 is a diagram of a system for reducing radiation scatter according to embodiments of the invention.

Referring now to FIG. 3, an embodiment includes an x-ray imaging system 100 having a radiation source 114, a detector 112, and a table 116. As shown, the radiation source 114 and the detector 112 are mounted on a C-shaped moveable arm 117 of a gantry 120. The housing 113 of the detector 112 includes an operational slot 121 configured to receive an anti-scatter grid. As will be appreciated, the operational slot 121 receives the grid that is being used during an active imaging procedure and also allows for subsequent removal of the grid being used. That is, the slot 121 may be configured with a latch or other mechanism, either mechanical or electrical, that may be easily and quickly actuated to allow a grid to be removed and replaced during operation.

Figure 4:
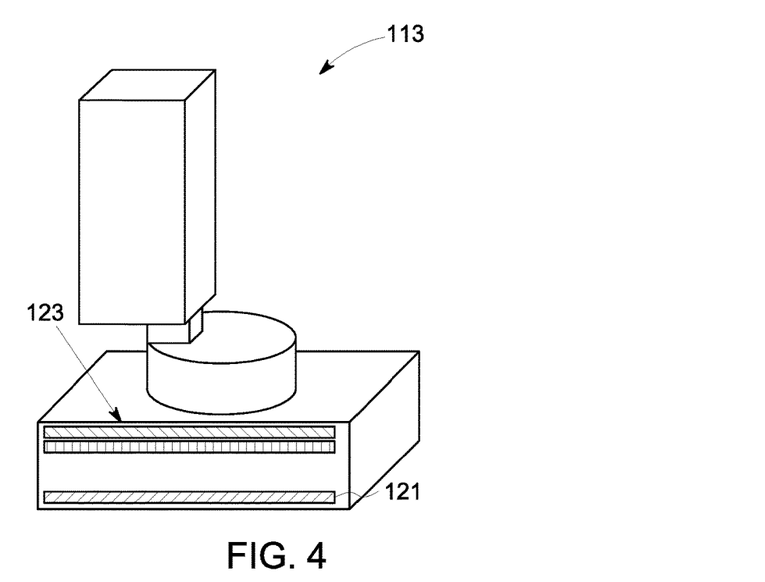
FIG. 4 is a diagram of a system for reducing radiation scatter according to a second embodiment of the invention.
Figure 5:
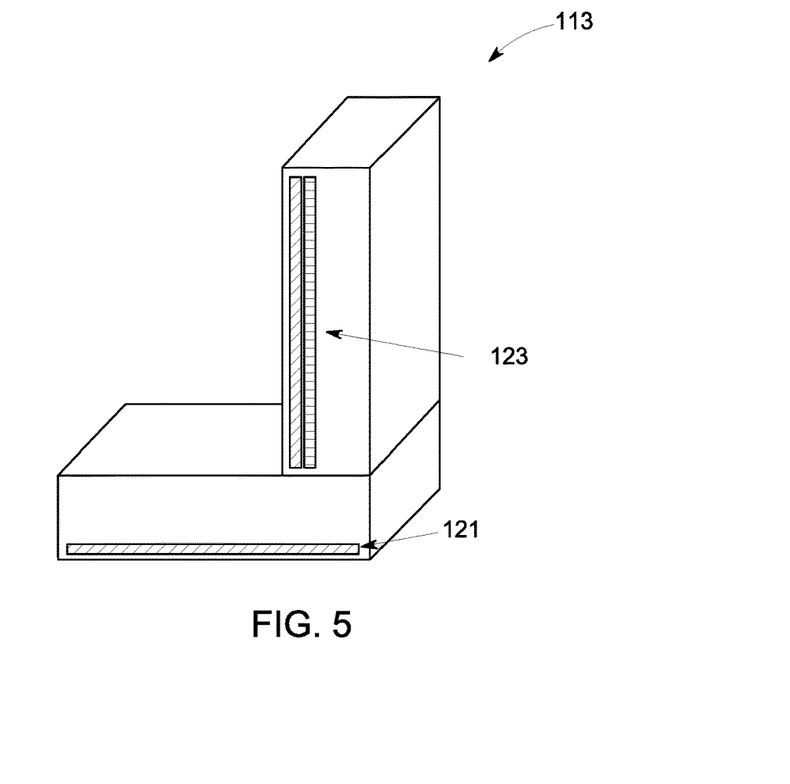
FIG. 5 is a diagram of a system for reducing radiation scatter according to a third embodiment of the invention.

The system 100 also includes one or more storage slots 123 that are formed in a component, or components, of the imaging system. As used herein, an "imaging system component" includes the table, the gantry, the radiation source, system housings, and all other equipment mechanically and/or electrically connected to the system or system controller. While the location of the storage slots 123 may vary, they should be easily accessible by an operator of the system. In embodiments, the storage slots 123 are located on a base portion of the system table 116 and/or on the gantry 120. The storage slots 123 may also be located in the radiation source housing 113 (FIGS. 4 and 5). As will be appreciated, however, the storage slots 123 may be formed in other operator accessible locations on the gantry 120 and need not be adjacent to one another. In certain embodiments, the storage slots 123 may be formed in separate, different system components. As mentioned, embodiments are not limited to any particular type or configuration of x-ray system, and are applicable to stationary or mobile systems and other imaging systems generally.

The storage slots 123 may be configured to store grids having imaging properties that differ from one another. As used herein, an "imaging property" of a grid includes the focal length, focal range, grid frequency, (i.e., grid rate and/or line rate), or grid ratio. The definition further includes other optical characteristics of a grid, such as a grid's transmission of primary radiation, transmission of scattered radiation and/or transmission of total radiation. Moreover, other parameters that can be derived from the transmission of radiation, such as grid contrast factor, selectivity, exposure factor (or Bucky factor), and quality factor are also imaging properties as used herein. Moreover, relevant optical grid characteristics set forth within the International Electrotechnical Commission's 60627 standard are included in the definition.

In depicted embodiments, there are two storage slots 123, which include a slot configured to receive and store a general-purpose grid 125 and one for a special purpose grid 127, such as a grid that has a focal length for use with CBCT imaging. In other embodiments, the number of slots may vary and may include a single slot or three or more slots each configured for a grid having a specific imaging property.

As will be appreciated, the dimensions of the slots may also vary based on the grids that they are configured to receive. For example, one of the slots may be larger than the other to accommodate a grid having a greater height. The slots should, however, securely hold the stored (or operational) grids in place such that they do not detrimentally move during operation and/or movement of the system and system components. In certain embodiments, the slots may include internal or external lights to guide insertion of grids, or, as discussed below, provide the operator with alerts regarding, for example, grid alignment, grid location, or the appropriateness of a particular grid in view of a selected imaging mode.

Embodiments of the invention further include a grid identification system in which the grid slots 121, 123, include sensors, e.g., readers, which are operatively connected to a processor/controller, such as controller 26, such that the sensors are in electrical communication with the same. The sensors are configured to detect both the presence/absence of a grid in one of the slots 121, 123, and also the type of grid, e.g., the optical properties of the grid such as the focal length thereof, in slots 121, 123. The sensors can then communicate the detected information regarding presence and type of grid to the processor/controller, which can then notify an operator of the appropriateness of a particular grid for a particular imaging mode. As will be appreciated, sensors may be present in one or more slots, or in all slots. In certain embodiments, the sensors may be located adjacent to, or in close proximity to the slots, as opposed to within the slots themselves. In certain embodiments, the system includes both storage slot sensors and an operational slot sensor.

The grids include a device that enables the system to assess an imaging property of the grid via the sensors. For example, the grids may include a passive RFID tag or label containing information on an imaging property, such as grid focal length. As will be appreciated, in such embodiments, the system would further include an RFID reader, or multiple readers, which would function as the sensor, as well as an antenna. The RFID readers could be located within or in proximity to the slots, or in another location on a system component. In other embodiments, the grids may include barcodes, e.g., QR or UPC, or other optical machine-readable representations of data. These systems would utilize one or more barcode readers, or other reader/scanner, located within or in proximity to the slots.

In yet other embodiments, the slots may contain a proximity sensor, such as an IR sensor. The proximity sensor could be used to assess whether a grid is inserted and/or whether it is aligned. Moreover, certain embodiments may combine several types of sensors, e.g., passive RFID and IR. In addition to the above, the system may generally utilize mechanical, electrical, magnetic grid detection/identification devices or means. In aspects, a passive identification device, e.g., RFID, is utilized, however, the invention is not so limited, and semi-passive or active devices may potentially be utilized.

In use, an operator can select an imaging mode, such as imaging a child or other imaging not requiring a grid, general interventional imaging, CBCT imaging, or other imaging criteria. Such other imaging criteria may include, but are not limited to, patient characteristics, ionizing radiation dose constraints, specific image quality needs, geometry/SID distance, and the like. Accordingly, "imaging mode" as used herein includes, but is not limited to, the aforementioned imaging modes and other imaging criteria.

Once selected, the controller 26 can then activate a sensor in the operational grid slot 121 to assess a "parameter" of the operational slot. The parameter can be the presence of and/or one or more imaging properties of the grid. That is, the controller 26 can determine whether an anti-scatter grid is in the slot 121. If there is no grid loaded, the controller 26 can alert the operator via the display screen 18, or other interface, to insert the appropriate grid. If a grid is in the slot 121, the sensor can then determine whether the grid type, e.g., the imaging properties thereof, matches the type that has been predetermined to be appropriate for the selected imaging mode.

As used herein, an "appropriate" grid refers to an anti-scatter grid that reduces radiation scatter to provide acceptable image quality for a given imaging mode, or other imaging criteria, or is otherwise linked or associated with a specific mode. As will be appreciated, in certain imaging modes, e.g., imaging a child, the appropriate grid type can be no grid. In embodiments, the appropriate grid type may be predetermined by inclusion or entry in a lookup table or algorithm executable by the controller 26. For example, for a specific mode, a quantitative value or range of values for an operational slot parameter assessed by the present invention may be predetermined as appropriate for a mode. In embodiments, this parameter may be focal length of a grid in a slot. As such, for example, a grid having a focal length of 100 cm may be predetermined as appropriate for a general-purpose imaging mode.

In an embodiment, when the operator has selected general-purpose imaging mode, for example, the controller, via the sensor, can determine whether a general-purpose anti-scatter grid is in operational slot 121. If it is not, the controller 26 can alert the operator via, for example, the display screen 18 to replace the loaded grid with the appropriate grid type. In a child mode, where no grid is utilized, the controller 26 can alert the operator if a grid is detected and instruct the operator to remove the same. Likewise, if a CBCT mode is selected, the sensor will determine whether a CBCT specific grid is in the operational slot 121.

With respect to alerts, the system 100 may also include one or more lights 140 located in or adjacent to the operational and storage slots 121, 123. Such lights may be used to alert an operator that, for example, a grid is misaligned, the slot contains an appropriate grid, or that the slot contains a grid that is inappropriate for a selected imaging mode. In one embodiment, the system provides an alert for the insertion of an appropriate grid within the operational slot, an alert for an inappropriate grid in the operational slot, and an alert that informs an operator of the location, e.g., a specific storage slot, of a grid that has been determined to be appropriate for insertion in the operational slot. These lights 140 can, for example, include green and red lights to indicate whether an appropriate or inappropriate grid is in the operational slot, respectively. The lights 140 can further include a flashing green light to indicate a storage slot contains a grid that is to be inserted for use for a selected imaging mode. Likewise, a flashing red light can indicate a storage slot contains a grid that is not to be utilized for a particular imaging study.

As will be readily appreciated, various colors and color combinations may be utilized, and, in certain embodiments, the lights 140 may also flash or pulse at different rates to provide a visual alert to the operator of a particular state or condition of the system. For example, the system may also provide visual alerts if a grid is damaged. The lights may include multiple lights of different colors or a single light per each slot that is capable of generating multiple colors.

In addition to providing alerts via the lights 140 mentioned above, the system may also provide alerts via the imaging monitor 18. Moreover, audible indicators, including tones, alarms, and synthesized voice messages may also be utilized. Textual messages or graphic indicators, e.g., icons, characters, etc., may also be provided on the imaging monitor or other display screen connected to a system component. In certain embodiments, a vibrational alert may also be provided.

Figure 6:
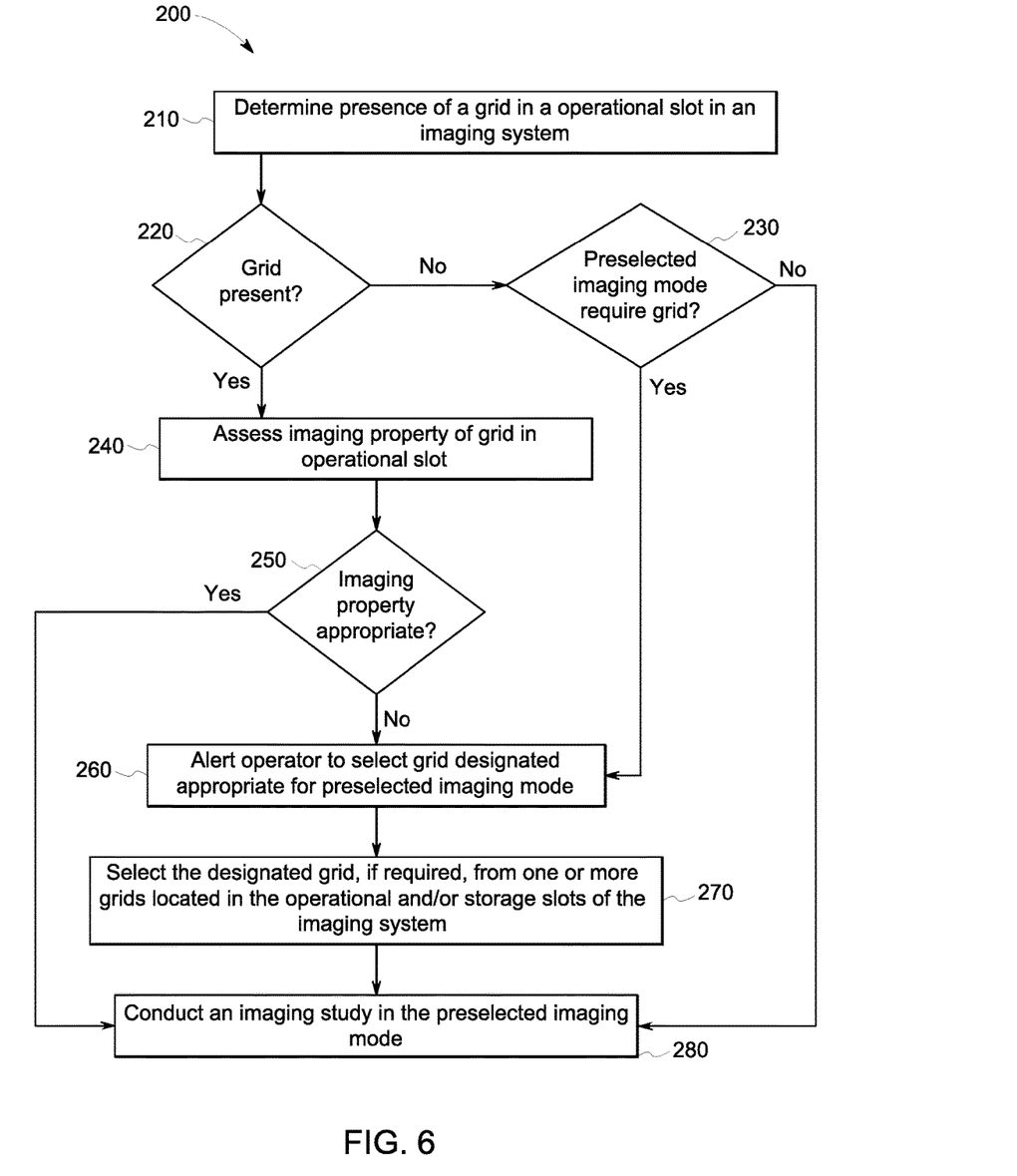
FIG. 6 is flowchart of a method of reducing radiation scatter in an imaging system according to an embodiment of the invention.

Referring now to FIG. 6, a flowchart graphically depicts a method 200 of the present invention. At an initial step, the presence of a grid in an operational slot is determined 210, 220, 230. If a grid is present, then an imaging property, e.g., focal length of the device, is assessed 240 and then compared to an imaging property that has previously been determined to be appropriate for the preselected imaging mode 250. If appropriate, the study may be conducted 280. If the imaging property of the grid is not appropriate for the preselected imaging mode, then a determination is made by the system as to the appropriate grid and an alert is generated for the operator to select the appropriate grid 260. At this point, an operator may then select the determined grid from among one or more grids located in storage or operational slots of the imaging system 270. If there is no grid in the operational slot, then a determination is made as to whether the preselected imaging mode requires a grid 230. If it does not, the study may then be conducted 280. If it does, however, then an alert is generated to the operator to select the appropriate grid 260. As will be appreciated, the grid may then be selected 270 and the study may commence 280.

It is to be understood that the imaging system 10 may include the necessary electronics, software, memory, storage, databases, firmware, logic/state machines, microprocessors, communication links, displays or other visual or audio user interfaces, printing devices, and any other input/output interfaces to perform the functions described herein and/or to achieve the results described herein. For example, the imaging system 10 may include at least one processor 30, system memory 32 including random access memory (RAM) and read-only memory (ROM), an input/output controller, and one or more data storage structures. All of these latter elements may be in communication with the at least one processor 30 to facilitate the operation of the imaging system 10 as discussed above. Suitable computer program code may be provided for executing numerous functions, including those discussed above in connection with the imaging system 10 and methods disclosed herein. The computer program code may also include program elements such as an operating system, a database management system and "device drivers" that allow the imaging system 10, to interface with computer peripheral devices (e.g., sensors, a video display, a keyboard, a computer mouse, etc.).

In embodiments, the instructions of the computer program code may be read into a main memory of a processor from a computer-readable medium. While execution of sequences of instructions in the program causes the processor to perform the process steps described herein, hard-wired circuitry may be used in place of, or in combination with, software instructions for implementation of the processes of the present invention. Thus, embodiments of the present invention are not limited to any specific combination of hardware and software.

The term "computer-readable medium" as used herein refers to any medium that provides or participates in providing instructions to at least one processor of the imaging system 10 (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, a RAM, a PROM, an EPROM or EEPROM (electronically erasable programmable read-only memory), a FLASH-EEPROM, any other memory chip or cartridge, or any other medium from which a computer can read.

Various forms of computer readable media may be involved in carrying one or more sequences of one or more instructions to at least one processor 30 for execution. For example, the instructions may initially be borne on a magnetic disk of a remote computer, e.g., a PC, (not shown).

In an aspect of the invention, an apparatus for reducing radiation scatter in an imaging system, having an operational slot for receiving an anti-scatter grid, includes an imaging system component having at least one storage slot formed therein for selectively storing an anti-scatter grid when the grid is not in the operational slot of the imaging system. The apparatus further includes an operational slot sensor configured to detect the presence of an anti-scatter grid and/or an imaging property of a grid in the operational slot. The system allows an operator to select an appropriate anti-scatter grid for use in the imaging system from one or more anti-scatter grids that are located within the operational and/or storage slots of the imaging system. In embodiments, the anti-scatter grids are two or more anti-scatter grids having different imaging properties which can be one or more of a focal length, focal range, grid frequency or grid ratio of the anti-scatter grids. The at least one storage slot can include a first storage slot for receiving a general-purpose anti-scatter grid and a second storage slot for receiving a CBCT grid. A controller operatively connected to the imaging system is included such that the controller is configured to assess a preselected imaging mode of the system, determine an anti-scatter grid appropriate for the preselected imaging mode, and assess whether the appropriate anti-scatter grid is in the operational slot of the system. The controller can provide an alert to an operator indicating whether or not an anti-scatter grid in the operational slot is appropriate for a selected imaging mode. In embodiments, a storage slot sensor configured to detect the presence of an anti-scatter grid and/or an imaging property of an anti-scatter grid in the storage slot. The controller provides an alert to an operator identifying which operational or storage slot contains an anti-scatter grid appropriate for the preselected imaging mode. The operational and/or storage slot sensors are RFID readers.

In another aspect, an imaging system includes a radiation source, a radiation detector and an operational slot located between the radiation source and radiation detector, the operational slot configured to receive an anti-scatter grid. The system further includes at least one storage slot formed in a imaging system component, the storage slot configured to receive and store an anti-scatter grid when the device is not in use in the operational slot and an operational slot sensor configured to detect the presence of an anti-scatter grid and/or an imaging property of a grid in the operational slot. The system allows an operator to select an appropriate anti-scatter grid from one or more anti-scatter grids that are located within the operational and/or storage slots of the imaging system. In an embodiment, the anti-scatter grids are two or more anti-scatter grids having different imaging properties and different imaging property is one or more of a focal length, focal range, grid frequency or grid ratio of the anti-scatter grids. The at least one storage slot includes a first storage slot for receiving a general-purpose anti-scatter grid and a second storage slot for receiving a CBCT grid. The system also includes a controller operatively connected to the imaging system such that the controller is configured to assess a preselected imaging mode of the system, determine an anti-scatter grid appropriate for the preselected imaging mode, and assess whether the appropriate anti-scatter grid is in the operational slot of the system. The controller provides an alert to an operator indicating whether or not an anti-scatter grid in the operational slot is appropriate for a selected imaging mode. In embodiments, the system includes a storage slot sensor configured to detect the presence of an anti-scatter grid and/or an imaging property of an anti-scatter grid in the storage slot so that the controller can provide an alert to an operator identifying which operational or storage slot contains the anti-scatter grid appropriate for the preselected imaging mode. The operational slot and/or storage slot sensor may be an RFID reader.

In an embodiment, a method of reducing radiation scatter in an imaging system having operational and storage slots for selectively receiving anti-scatter grids includes assessing a parameter of an operational slot via an operational slot sensor, determining whether the assessed parameter is appropriate for a preselected imaging mode of the imaging system, and selecting an appropriate anti-scatter grid, if required, from one or more anti-scatter grids located in the operational and/or storage slots of the imaging system, based on the assessed parameter. The method includes conducting an imaging study in the preselected imaging mode using the appropriate anti-scatter grid and the parameter includes whether an anti-scatter grid is located in the operational slot and/or an imaging property of an anti-scatter grid located in the operational slot. The imaging property is one or more of a focal length, focal range, grid frequency or grid ratio of the anti-scatter grids. The method further includes providing an alert to an operator of the system as to whether the assessed parameter is appropriate for a preselected imaging mode of the imaging system. The method may also include providing an alert to an operator of the system identifying which operational or storage slot contains the anti-scatter grid appropriate for the preselected imaging mode. The alert is a visual or audible indicator and can include an activation of a light in proximity to the operational or storage slot that contains the appropriate anti-scatter grid. The method further includes providing an alert to an operator of the system indicating that an anti-scatter grid is misaligned within an operational or storage slot of the system.

Further, while the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their objects. Further, the limitations of the following claims are not written in means-plus-function format are not intended to be interpreted based on 35 U.S.C. § 112(f), unless and until such claim limitations expressly use the phrase "means for" followed by a statement of function void of further structure.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described invention, without departing from the spirit and scope of the invention herein involved, it is intended that all of the subject matter of the above description shown in the accompanying drawings shall be interpreted merely as examples illustrating the inventive concept herein and shall not be construed as limiting the invention.

What is claimed is:

1. An apparatus for reducing radiation scatter in an imaging system, the imaging system including an operational slot for receiving an anti-scatter grid, the apparatus comprising:
   an imaging system component having at least one storage slot formed therein for selectively storing an anti-scatter grid when the grid is not in the operational slot of the imaging system;
   an operational slot sensor configured to detect the presence of an anti-scatter grid and/or an imaging property of a grid in the operational slot; and
   wherein the system allows an operator to select an appropriate anti-scatter grid for use in the imaging system from one or more anti-scatter grids that are located within the operational and/or storage slots of the imaging system.

2. The apparatus of claim 1 wherein the anti-scatter grids are two or more anti-scatter grids having different imaging properties.

3. The apparatus of claim 2 wherein the different imaging property is one or more of a focal length, focal range, grid frequency or grid ratio of the anti-scatter grids.

4. The apparatus of claim 1 wherein the at least one storage slot includes a first storage slot for receiving a general-purpose anti-scatter grid and a second storage slot for receiving a CBCT grid.

5. The apparatus of claim 1 further comprising:
   a controller operatively connected to the imaging system such that the controller is configured to assess a preselected imaging mode of the system, determine an anti-scatter grid appropriate for the preselected imaging mode, and assess whether the appropriate anti-scatter grid is in the operational slot of the system.

6. The apparatus of claim 5 wherein the controller provides an alert to an operator indicating whether or not an anti-scatter grid in the operational slot is appropriate for a selected imaging mode.

7. The apparatus of claim 5 further comprising:
   a storage slot sensor configured to detect the presence of an anti-scatter grid and/or an imaging property of an anti-scatter grid in the storage slot; and
   wherein controller provides an alert to an operator identifying which operational or storage slot contains an anti-scatter grid appropriate for the preselected imaging mode.

8. The apparatus of claim 1 wherein the operational slot sensor is an RFID reader configured to read data contained on an anti-scatter grid.

9. The apparatus of claim 7 wherein the storage slot sensor is an RFID reader configured to read data contained on an anti-scatter grid.

10. An imaging system comprising:
    a radiation source;
    a radiation detector;
    an operational slot located between the radiation source and radiation detector, the operational slot configured to receive an anti-scatter grid;
    at least one storage slot formed in a imaging system component, the storage slot configured to receive and store an anti-scatter grid when the device is not in use in the operational slot;
    an operational slot sensor configured to detect the presence of an anti-scatter grid and/or an imaging property of a grid in the operational slot; and
    wherein the system allows an operator to select an appropriate anti-scatter grid from one or more anti-scatter grids that are located within the operational and/or storage slots of the imaging system.

11. The system of claim 10 wherein the anti-scatter grids are two or more anti-scatter grids having different imaging properties.

12. The system of claim 11 wherein the different imaging property is one or more of a focal length, focal range, grid frequency or grid ratio of the anti-scatter grids.

13. The system of claim 10 wherein the at least one storage slot includes a first storage slot for receiving a general-purpose anti-scatter grid and a second storage slot for receiving a CBCT grid.

14. The system of claim 10 further comprising:
    a controller operatively connected to the imaging system such that the controller is configured to assess a preselected imaging mode of the system, determine an anti-scatter grid appropriate for the preselected imaging mode, and assess whether the appropriate anti-scatter grid is in the operational slot of the system.

15. The system of claim 14 wherein the controller provides an alert to an operator indicating whether or not an anti-scatter grid in the operational slot is appropriate for a selected imaging mode.

16. The system of claim 14 further comprising:
    a storage slot sensor configured to detect the presence of an anti-scatter grid and/or an imaging property of an anti-scatter grid in the storage slot; and
    wherein controller provides an alert to an operator identifying which operational or storage slot contains the anti-scatter grid appropriate for the preselected imaging mode.

17. The system of claim 10 wherein the operational slot sensor is an RFID reader configured to read data contained on an anti-scatter grid.

18. The system of claim 16 wherein the storage slot sensor is an RFID reader configured to read data contained on an anti-scatter grid.

19. A method of reducing radiation scatter in an imaging system having operational and storage slots for selectively receiving anti-scatter grids, the method comprising:
    assessing a parameter of an operational slot via an operational slot sensor;
    determining whether the assessed parameter is appropriate for a preselected imaging mode of the imaging system; and
    selecting an appropriate anti-scatter grid, if required, from one or more anti-scatter grids located in the operational and/or storage slots of the imaging system, based on the assessed parameter.

20. The method of claim 19 further comprising:
conducting an imaging study in the preselected imaging mode using the appropriate anti-scatter grid.

21. The method of claim 19 wherein the parameter includes whether an anti-scatter grid is located in the operational slot and/or an imaging property of an anti-scatter grid located in the operational slot.

22. The method of claim 21 wherein the imaging property is one or more of a focal length, focal range, grid frequency or grid ratio of the anti-scatter grids.

23. The method of claim 19 further comprising:
providing an alert to an operator of the system as to whether the assessed parameter is appropriate for a preselected imaging mode of the imaging system.

24. The method of claim 19 further comprising:
providing an alert to an operator of the system identifying which operational or storage slot contains the anti-scatter grid appropriate for the preselected imaging mode.

25. The method of claim 24 wherein the alert is a visual or audible indicator.

26. The method of claim 24 wherein the alert includes an activation of a light in proximity to the operational or storage slot that contains the appropriate anti-scatter grid.

27. The method of claim 19 further comprising:
providing an alert to an operator of the system indicating that an anti-scatter grid is misaligned within an operational or storage slot of the system.

* * * * *